(12) United States Patent  
Tracey et al.

(10) Patent No.: US 7,647,112 B2  
(45) Date of Patent: Jan. 12, 2010

(54) SYSTEM AND METHOD FOR SELECTIVELY STIMULATING DIFFERENT BODY PARTS

(75) Inventors: Michael R. Tracey, Branchburg, NJ (US); Anthony DiUbaldi, Jackson, NJ (US); Douglas B. Johns, Milford, NJ (US)

(73) Assignee: Ethicon, Inc., Somerville, NJ (US)

( * ) Notice: Subject to any disclaimer, the term of this patent is extended or adjusted under 35 U.S.C. 154(b) by 697 days.

(21) Appl. No.: 11/344,285

(22) Filed: Jan. 31, 2006

(65) Prior Publication Data

US 2006/0195146 A1 Aug. 31, 2006

Related U.S. Application Data

(63) Continuation-in-part of application No. 11/146,522, filed on Jun. 7, 2005, which is a continuation-in-part of application No. 11/043,830, filed on Jan. 26, 2005, now abandoned.

(60) Provisional application No. 60/543,722, filed on Feb. 11, 2004.

(51) Int. Cl.  
*A61N 1/36* (2006.01)

(52) U.S. Cl. .............. 607/41; 607/2; 607/39; 607/40; 607/115

(58) Field of Classification Search ........ 607/1–3, 607/40, 41, 115–118, 142, 148, 153; 600/372, 600/373; 606/36, 41, 43  
See application file for complete search history.

(56) References Cited

U.S. PATENT DOCUMENTS

| 3,683,915 | A | | 8/1972 | Voss |
| 4,406,288 | A | | 9/1983 | Horwinski et al. |
| 5,047,028 | A | * | 9/1991 | Qian ............ 606/49 |
| 5,167,237 | A | | 12/1992 | Rabin et al. |
| 5,350,414 | A | | 9/1994 | Kolen |
| 5,458,630 | A | * | 10/1995 | Hoegnelid et al. ........ 607/116 |

(Continued)

FOREIGN PATENT DOCUMENTS

EP 0783267 B1 2/1999

(Continued)

OTHER PUBLICATIONS

Walter et al, "Evaluation of a 316LVM Woven Eye Electrode for Direct Bladder Stimulation", *Engineering in Medicine and Biology Society 1991*, vol. 13:1991, Proceedings of the Annual International Conference of the IEEE Orlando, FL, USA, Oct. 31-Nov. 3, 1991, New York, NY, USA, IEEE, US, Oct. 31, 1991, pp. 1853-1854.

(Continued)

*Primary Examiner*—Carl H Layno  
*Assistant Examiner*—Pamela M Bays

(57) ABSTRACT

Devices and methods are provided for electrically stimulating a predetermined body part of a mammal. The method includes placing at least one electrode in proximity to the mammal's skin, injecting an electrically conductive gel into the body of the mammal so as to form a conductive gel pathway extending at least partially along a distance between the at least one electrode and the predetermined body part, and stimulating the predetermined body part by applying an electrical signal via the electrode that travels, at least in part, through the conductive gel pathway.

15 Claims, 14 Drawing Sheets

U.S. PATENT DOCUMENTS

| | | | |
|---|---|---|---|
| 5,464,434 | A | 11/1995 | Alt |
| 5,556,421 | A | 9/1996 | Prutchi et al. |
| 5,558,640 | A | 9/1996 | Pfeiler et al. |
| 5,562,717 | A | 10/1996 | Tippey et al. |
| 5,617,876 | A | 4/1997 | van Duyl |
| 5,645,062 | A | 7/1997 | Anderson et al. |
| 5,702,428 | A | 12/1997 | Tippey et al. |
| 5,722,996 | A | 3/1998 | Bonnet et al. |
| 5,730,125 | A | 3/1998 | Prutchi et al. |
| 5,735,887 | A | 4/1998 | Barreras, Sr. et al. |
| 5,791,344 | A | 8/1998 | Schulman et al. |
| 5,851,223 | A | 12/1998 | Liss et al. |
| 5,902,328 | A * | 5/1999 | LaFontaine et al. ......... 607/116 |
| 5,911,223 | A * | 6/1999 | Weaver et al. ............... 128/898 |
| 5,993,414 | A | 11/1999 | Haller |
| 6,092,530 | A | 7/2000 | Weissman et al. |
| 6,099,479 | A | 8/2000 | Christopherson et al. |
| 6,155,267 | A | 12/2000 | Nelson |
| 6,164,284 | A | 12/2000 | Schulman et al. |
| 6,183,461 | B1 | 2/2001 | Matsuura et al. |
| 6,199,575 | B1 | 3/2001 | Widner |
| 6,205,359 | B1 | 3/2001 | Boveja |
| 6,221,024 | B1 | 4/2001 | Miesel |
| 6,231,516 | B1 | 5/2001 | Keilman et al. |
| 6,240,317 | B1 | 5/2001 | Villaseca et al. |
| 6,263,246 | B1 | 7/2001 | Goedeke et al. |
| 6,285,897 | B1 | 9/2001 | Kilcoyne et al. |
| 6,330,885 | B1 | 12/2001 | Weissman et al. |
| 6,354,991 | B1 | 3/2002 | Gross et al. |
| 6,360,129 | B1 | 3/2002 | Ley et al. |
| 6,384,353 | B1 | 5/2002 | Huang et al. |
| 6,402,689 | B1 | 6/2002 | Scarantino et al. |
| 6,404,204 | B1 | 6/2002 | Farruggia et al. |
| 6,413,393 | B1 | 7/2002 | Van Antwerp et al. |
| 6,432,050 | B1 | 8/2002 | Porat et al. |
| 6,438,407 | B1 | 8/2002 | Ousdigian et al. |
| 6,442,413 | B1 | 8/2002 | Silver |
| 6,447,462 | B1 | 9/2002 | Wallace et al. |
| 6,449,512 | B1 * | 9/2002 | Boveja ......................... 607/41 |
| 6,471,645 | B1 | 10/2002 | Warkentin et al. |
| 6,497,655 | B1 | 12/2002 | Linberg et al. |
| 6,505,074 | B2 | 1/2003 | Boveja et al. |
| 6,535,766 | B1 | 3/2003 | Thompson et al. |
| 6,652,449 | B1 | 11/2003 | Gross et al. |
| 6,662,052 | B1 | 12/2003 | Sarwal et al. |
| 6,668,191 | B1 * | 12/2003 | Boveja ......................... 607/2 |
| 6,712,772 | B2 | 3/2004 | Cohen et al. |
| 6,862,480 | B2 | 3/2005 | Cohen et al. |
| 2001/0025137 | A1 | 9/2001 | Webb et al. |
| 2001/0051768 | A1 | 12/2001 | Schulman et al. |
| 2002/0001870 | A1 | 1/2002 | Oda et al. |
| 2002/0011592 | A1 | 1/2002 | Matsuo |
| 2002/0026141 | A1 | 2/2002 | Houben et al. |
| 2002/0026244 | A1 | 2/2002 | Trieu |
| 2002/0082480 | A1 | 6/2002 | Riff et al. |
| 2002/0103514 | A1 | 8/2002 | Abrahamson |
| 2002/0107540 | A1 | 8/2002 | Whalen et al. |
| 2002/0111542 | A1 | 8/2002 | Warkentin et al. |
| 2002/0133196 | A1 | 9/2002 | Thompson |
| 2002/0151816 | A1 | 10/2002 | Rich et al. |
| 2003/0004403 | A1 | 1/2003 | Drinan et al. |
| 2003/0004553 | A1 | 1/2003 | Grill et al. |
| 2003/0220669 | A1 | 11/2003 | Shealy |
| 2004/0015223 | A1 * | 1/2004 | Andino et al. ............... 607/142 |
| 2004/0068203 | A1 | 4/2004 | Gellman et al. |
| 2004/0236194 | A1 | 11/2004 | Meyer |
| 2005/0154434 | A1 * | 7/2005 | Simon et al. ................. 607/116 |
| 2005/0177067 | A1 | 8/2005 | Tracey et al. |
| 2005/0277998 | A1 | 12/2005 | Tracey et al. |
| 2006/0195146 | A1 | 8/2006 | Tracey et al. |

FOREIGN PATENT DOCUMENTS

| | | |
|---|---|---|
| EP | 1048264 A1 | 11/2000 |
| WO | WO 90/14127 A | 11/1990 |
| WO | WO 97/18856 A1 | 5/1997 |
| WO | WO 97/39796 A1 | 10/1997 |
| WO | WO 99/55411 A2 | 11/1999 |
| WO | WO 0033738 A1 | 5/2000 |
| WO | WO 00/33065 A1 | 6/2000 |
| WO | WO 01/49369 A1 | 7/2001 |
| WO | WO 01/56633 A2 | 8/2001 |
| WO | WO 02/22008 A1 | 3/2002 |
| WO | WO 02/27294 A1 | 4/2002 |
| WO | WO 02/058551 A3 | 8/2002 |
| WO | WO 02/062215 A2 | 8/2002 |
| WO | WO 03/015625 A1 | 2/2003 |
| WO | WO 03/020364 A2 | 3/2003 |
| WO | WO 03/030733 A | 4/2003 |
| WO | WO 03/071944 A1 | 9/2003 |
| WO | WO 2004/050172 A | 6/2004 |
| WO | WO 2005/002663 A2 | 1/2005 |

OTHER PUBLICATIONS

Siwapornsathain, E. et al., "Telemetry and Sensor Platform for Ambulatory Urodynamics", Proceedings of the $2_{nd}$ Annual International IEEE-EMBS Special Topica Conference on Microtechnologies in Medicine & Biology, Madison, WI, May, (2002).

Rousche, P.J. et al. "Flexible Polyimide-Based Intracortical Electrode Arrays with Bioactive Capability", IEEE Transactions on Biomedical Engineering, vol. 48, No. 3 (2001).

Becker, T.J. "CardioMEMS Moves Closer to Commercializing Its Innovative Heart Sensors", (1905) ATDC News & Information, Georgia Institute of Technology.

Voskerician, G. et al., "Biocompatibility and biofouling of MEMS drug delivery devices" Biomaterials, 24, 1959-1967 (2003).

Fiber Optic Sensors, Product Datasheet FOP-M Pressure sensor (undated).

Chappell, J. Electronic News—Ambient Intelligence (2002).

* cited by examiner

FIG. 12a
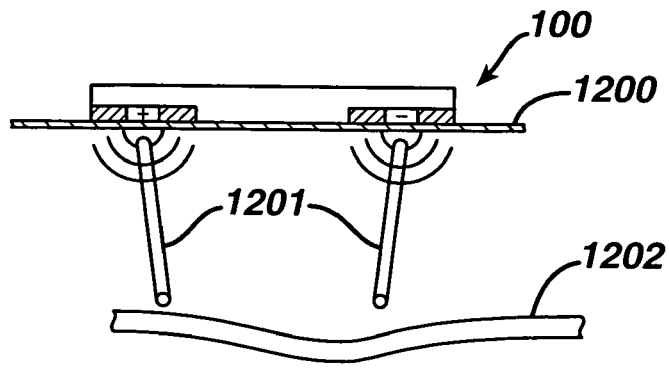
FIG. 12b
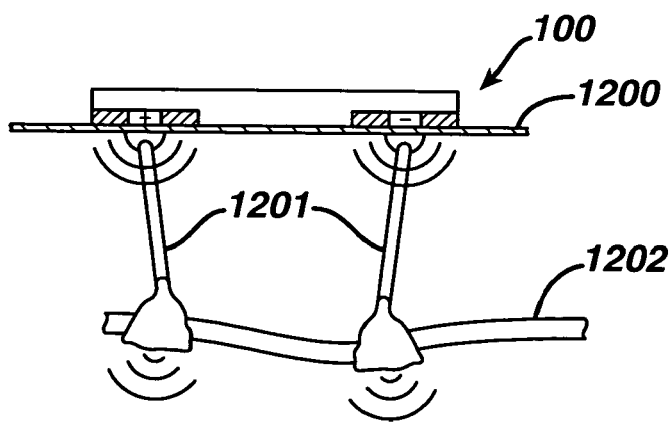
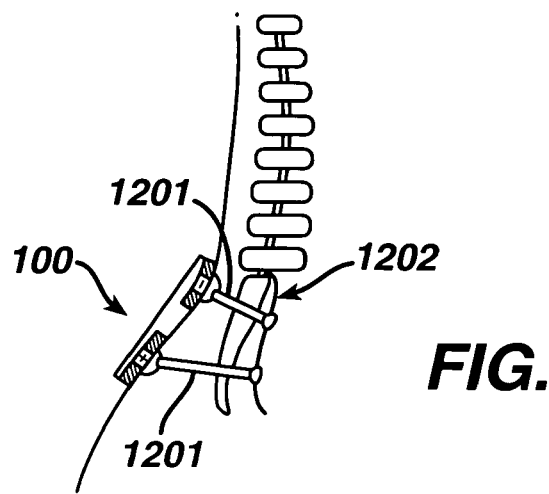
FIG. 12c

SYSTEM AND METHOD FOR SELECTIVELY STIMULATING DIFFERENT BODY PARTS

CROSS-REFERENCE TO RELATED APPLICATIONS

The present application a continuation-in-part of U.S. patent application Ser. No. 11/146,522, filed on Jun. 7, 2005, which is a continuation-in-part of U.S. patent application Ser. No. 11/043,830, filed on Jan. 26, 2005, now abandoned which claims priority to U.S. provisional patent application Ser. No. 60/543,722, filed on Feb. 11, 2004.

BACKGROUND OF THE INVENTION

1. Field of the Invention

The present invention relates generally to devices and methods for selectively stimulating parts of the body, and more particularly to devices and method for selectively stimulating various nerves or selectively applying electrical stimulation to various other body parts.

2. Background Discussion

Women account for more than 11 million incontinence cases. One type of incontinence is stress urinary incontinence (SUI), where women experience involuntary loss of urine during normal daily activities and movements, such as laughing, coughing, sneezing and regular exercise. SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Where stress incontinence is typically a result of an anatomical defect, another form of incontinence, urge incontinence, appears to be neurologically based and generally revealed as detrusor muscle instability or "bladder spasms." As such it is usually not conducive to surgical correction. Urge incontinence may or may not result in urine leakage, but both conditions otherwise have similar symptoms and similar forms of treatment, which generally include a combination of behavioral modification (learned strategies for reducing the urge sensation, scheduled voiding, avoidance of bladder-stimulating substances such as caffeine, and pelvic muscle exercises, with or without biofeedback) and drug therapy (typically anticholinergeic agents such as oxybutynin or tolterodine). These treatments require life-long therapy. Unfortunately, behavioral modification requires continuous effort to maintain results and the available drugs have significant side effects for many patients causing 80% to discontinue therapy within a year. The alternative therapy is to modify lifestyle to accommodate the condition—frequent urination to avoid "accidents" and wearing protective pads or undergarments, depending on the severity of the condition.

Another approach for treatment is stimulation of the sacral and/or pudendal nerve. The sacral spinal nerve roots separate in pairs to exit laterally through the nerve root foramina. The main destinations for these roots are the sacral plexus. Nerves from this plexus provide the motor and sensory innervation of the lower limbs and pelvic organs. Specifically, the sacral plexus splits into five sacral nerve pair, sacral spinal nerves S1 to S5. These nerves supply the thighs and lower parts of the legs, the feet, most of the external genital organs, and the area around the anus. The pudendal nerve is the largest branch of the pudendal plexus and is composed of somatosensory, somatomotor and autonomic elements derived from the anterior primary divisions of the second, third and fourth sacral nerves. The pudendal nerve affects the function of the bladder, urethral sphincter and genitals. Lower branches of the pudendal nerve contribute to peristalsis of the colon and anal sphincter contraction force. The pudendal nerve is closer to the bladder, and its stimulation innervates the bladder, thus eliminating or lessening its contractions. At least one known commercial device stimulates the sacral nerve through a needle extended into the sacral nerve bundle. This device, however, supplies a continuous signal to provide constant stimulation of the nerve. Various drawbacks of this device include its invasive nature, and unwanted stimulation effects on other areas of the body, since the sacral nerve as a whole is being stimulated and multiple other areas of the body are innervated by such stimulation (i.e., resulting in leg twitches or the like).

A company called Advanced Bionics has an implantable stimulation device that targets the pudendal nerve specifically rather than the sacral nerve. This device is implanted in the vicinity of the pudendal nerve, but also is invasive and supplies a constant signal as described above and therefore, has the same drawbacks.

In addition to incontinence, women can suffer from other diseases as well, often simultaneously with incontinence. Interstitial cystitis is a chronic bladder condition involving an inflamed or irritated bladder wall. Patients with this condition may experience mild discomfort, pressure, tenderness, or intense pain in the bladder and surrounding pelvic area. Other symptoms may include an urgent need to urinate (urgency), frequent need to urinate (frequency), or a combination of these symptoms. The inflammation can lead to scarring and stiffening of the bladder, less bladder capacity (the bladder is able to hold less urine), and pinpoint bleeding in the bladder lining. In rare cases, ulcers form in the bladder lining. Of the more than 700,000 Americans estimated to have interstitial cystitis, about 90 percent are women.

Treatments for interstitial cystitis include oral medicines, such as aspirin, ibuprofen, other painkillers, antidepressants and antihistamines. Another treatment is bladder instillation (a bladder wash or bath) in which the bladder is filled with a solution that is held for varying periods of time before being emptied. These treatments require life-long therapy. Sacral nerve stimulation implants are also used for the treatment of interstitial cystitis, but, as stated previously, its invasive nature and unwanted stimulation effects on other areas of the body make this treatment undesirable. Surgery, considered a treatment of last resort, does not necessarily improve symptoms.

Other diseases that may occur simultaneously with urinary incontinence include fecal and anal incontinence. Fecal incontinence is the inability to control the bowels, and can have several causes with constipation being the most common. Fecal incontinence can also be caused by injury to one or both of the ring-like muscles at the end of the rectum called the anal internal and/or external sphincters. In women, the damage often happens when giving birth. Hemorrhoid surgery can damage the sphincters as well. Fecal incontinence can also be caused by damage to the nerves that control the anal sphincters or to the nerves that sense stool in the rectum. Nerve damage can also be caused by childbirth, a long-term habit of straining to pass stool, stroke, and diseases that affect the nerves, such as diabetes and multiple sclerosis. In addition, rectal surgery, radiation treatment, and inflammatory bowel disease can cause scarring that makes the walls of the rectum stiff and less elastic. Abnormalities of the pelvic floor, which is typically caused by childbirth, can also lead to fecal incontinence. Examples of some abnormalities are decreased perception of rectal sensation, decreased anal canal pressures, decreased squeeze pressure of the anal canal, impaired anal sensation, a dropping down of the rectum (rectal prolapse), protrusion of the rectum through the vagina (rectocele), and/or generalized weakness and sagging of the pelvic floor. Treatment depends on the cause and severity of fecal incontinence, and may include dietary changes, medication, bowel training, or surgery. A last resort is a colostomy, which is the surgical creation of an opening between the large intestine and the abdominal wall. More than one treatment may be necessary for successful control since continence is a complicated chain of events.

One type of treatment typically cannot be used to treat the different conditions described above, and, as indicated above, many of the known treatments are invasive or have other negative side effects. Accordingly, what is needed is an improved device and method for simultaneously treating different diseases or conditions.

SUMMARY OF THE INVENTION

The present invention provides devices and methods for electrically stimulating a predetermined body part of a mammal. The method includes placing at least one electrode in proximity to the mammal's skin, injecting an electrically conductive gel into the body of the mammal so as to form a conductive gel pathway extending at least partially along a distance between the at least one electrode and the predetermined body part, and stimulating the predetermined body part by applying an electrical signal via the electrode that travels, at least in part, through the conductive gel pathway. The conductive gel pathway may extend substantially the entire distance between the electrode and predetermined body part, and/or may substantially envelope the predetermined body part.

According to various embodiments, the conductive gel can be bio-inert, can remain flexible following injection, and may be a cross-linked polyacrylamide gel, or a thermoset hydrogel or thermoplastic hydrogel. The predetermined body part may be a nerve, such as the pudendal nerve.

In yet another embodiment, the predetermined body part is the pudendal nerve, and the placing step further includes placing the electrode in the abdominal or sacral regions of the mammal. In yet another embodiment, the electrode is positioned within a patch device having an adhesive thereon for securing it to the skin.

The injecting step may be performed using a syringe.

A method is also provided for electrically stimulating a pudendal or sacral nerve of a mammal, and includes placing at least one electrode in proximity to the mammal's skin substantially in the abdominal or sacral regions of the mammal, injecting an electrically conductive gel into the body of the mammal so as to form a conductive gel pathway extending at least partially along a distance from the at least one electrode to the pudendal or sacral nerve, and stimulating the pudendal or sacral nerve by applying an electrical signal via the electrode that travels, at least in part, through the conductive gel pathway.

Yet another method is provided for treating a pelvic condition of a female patient including providing a transcutaneous electrical stimulation device including an electrode adapted to apply an electrical waveform to the patient's skin, identifying a location for placing the stimulation device that is substantially in the patient's abdominal or sacral regions, creating a conductive pathway along at least a portion of a distance from the identified location to the patient's pudendal or sacral nerve by injecting a conductive gel along the pathway, placing the stimulation device in the identified location, and stimulating the pudendal or sacral nerve by activating the electrode to thereby apply the electrical waveform to the patient's skin, wherein the electrical waveforms is conducted, at least in part, through the conductive pathway.

The present invention further provides an electrical stimulation device for stimulating a selected internal body part of a mammal. The device includes at least one electrode adapted for placement in proximity to skin of the mammal and adapted to apply an electrical waveform thereto, and an electrically conductive gel pathway extending along at least a portion of a distance from the at least one electrode to the selected internal body part. The conductive gel pathway is a material selected from the group consisting of a poly(acrylamide), a thermoset hydrogel and a thermoplastic hydrogel.

According to one embodiment, the conductive gel includes a thermoset hydrogel selected from the group consisting of cross-linked varieties of polyHEMA and copolymers, N-substituted acrylamides, polyvinylpyrrolidone (PVP), poly(glyceryl methacrylate), poly(ethylene oxide), poly(vinyl alcohol), poly(acrylic acid), poly(methacrylic acid), poly(N,N-dimethylaminopropyl-N'-acrylamide), and combinations thereof with hydrophilic and hydrophobic comonomers, cross-linkers and other modifiers.

In an alternate embodiment, the conductive gel includes a thermoplastic hydrogel selected from the group consisting of acrylic derivatives, vinyl alcohol derivatives, hydrophilic polyurethanes (HPU) and Styrene/PVP block copolymers.

BRIEF DESCRIPTION OF THE DRAWINGS

FIGS. 2a and 2b illustrates exemplary waveforms generated by the devices of FIGS. 1 and 1a;

FIGS. 12a-c illustrate use of the transdermal transmission device in connection with a conductive gel tract.

DETAILED DESCRIPTION OF THE INVENTION

Figure 1:
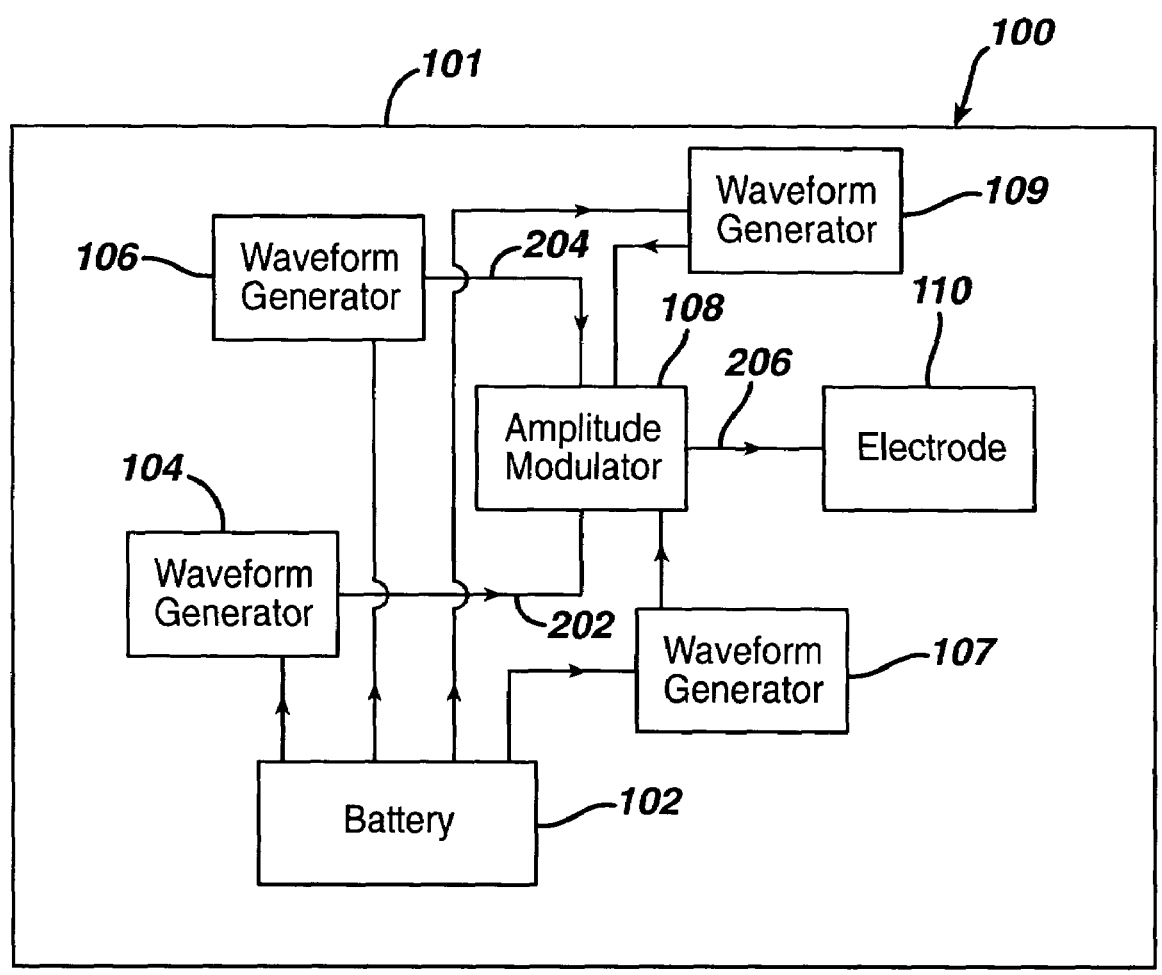
FIGS. 1 and 1a are schematic illustrations of transdermal transmission devices according to selected embodiments of the present invention.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described in detail in relation to nerve stimulation in females, it is to be understood that it can be readily adapted for use in males, and children as well as adults. The inventive principles, apparatus and methods disclosed herein may also have application for stimulating various other nerves, either independently or simultaneously, such as stimulation of nerves during labor and delivery, or selectively stimulating branches of a given nerve bundle to selectively address different patient conditions. Thus, the present invention can, for example, be used to selectively treat or affect one or more of the following conditions simultaneously: stress urinary incontinence, anal and fecal incontinence, sexual dysfunction, interstitial cystitis, chronic pain such as but not limited to pelvic pain, nocturia, and gastrointestinal disorders such as but not limited to gastric pacing. Finally, the present invention as described herein can also be used to stimulate body parts other than nerves, such as glands that secrete hormones, and large muscle groups, such as biceps muscle stimulation associated with physical therapy.

One unique aspect of the invention described herein is the manner in which the nerve(s) or other body parts are stimulated, which is transdermally rather than via a needle or other invasive element inserted within the body in close proximity to the nerve. This has obvious advantages in comfort for the patient, but also eliminates the surgical risk of mistakenly injuring other nerves or vessels. The system provides direct, but preferably selective stimulation to a nerve or the like that may be, if desired, controlled in part based on biofeedback data corresponding to physiological conditions sensed in the body, such as bladder contractions.

With regard to its application for stimulating nerves, an underlying principal of its operation is the fact that nerves within the body can be selectively targeted for stimulation without affecting adjacent neurons. As is well known to those skilled in the art, bioelectric potentials are produced as a result of electrochemical activity of excitable cells found within nervous system tissue. These excitable cells exist in two electrical states, resting potential or action potential. Cells remain in the resting potential state until adequate stimulus is provided to cause the cell to reach the action or threshold potential, at which time the nerve "fires," and the action potential travels at a constant conduction velocity unattenuated along the cell membranes. This all-or-nothing response of the action potential causes the cell's membrane potential to go through a characteristic repeatable cycle, where the potential first goes from the negative resting potential, to a positive action potential, and then back down to the negative resting potential again all within approximately 1 ms. The response remains the same regardless of the magnitude of the stimulus, so long as it exceeds the threshold potential.

As is also well known, when an excitable cell membrane has an action potential response (from an adequate stimulus), its ability to respond to a second stimulus is significantly altered. During the initial, depolarizing portion of the action potential, the cell membrane cannot respond to additional stimulus regardless of its intensity. This period is referred to as the absolute refractory period. Immediately following the absolute refractory period is the relative refractory period where the cell membrane can respond only to intense stimulation. The existence of the absolute and relative refractory periods results in an upper frequency limit at which a cell can be repeatedly discharged. Thus, neurons can be seen as frequency dependent devices. The frequency dependent component of the neuron depends on its total capacitance, which will vary from neuron to neuron and will be a function of its length, diameter, coating (myelination) and the permeativity of the dielectric medium. In other words, for any given dielectric medium, varying either the length or diameter of the neuron, or its myelination, will vary its total capacitance.

Since neurons in the human body do vary greatly in diameter, length and myelination, the capacitance and conduction velocity (operating frequency) for these neurons vary as well. Using these differences in physical characteristics of adjacent neurons, selected nerves can be targeted for stimulation without affecting adjacent neurons. That is, selective neural stimulation can be achieved by characterizing the frequency response (capacitance) of adjacent neurons, and tuning the stimulation frequency to an area of no-overlap. For example, consider two adjacent neurons, where neuron A has a frequency band of operation from 0-20 Hz, and neuron B has a frequency band of operation from 20-30 Hz. Thus, within the frequency band of 20-30 Hz, neuron B can be selectively stimulated with no effect on neuron A. Further, neuron A can be selectively stimulated even in an overlapping frequency range if stimulation is applied during neuron B's absolute refractory period, during which no amount of stimulation will cause neuron B to fire as discussed above, or if the stimulation is less than the magnitude required to cause stimulation during the relative refractory period. As described further below, these principles can be applied to achieve selective stimulation of two or more nerves within the body.

As indicated above, it is known that surface electrodes can be used to stimulate both nerves and muscles within the body. One problem that is encountered, however, is that the applied electrical signals tend to spread widely, affecting untargeted muscles and nerves as well as targeted ones, which is often undesirable. Further, to account for this signal dissipation, the applied current levels must be significantly increased to ensure adequate current densities at the targeted site. Another challenge associated with transdermal application of electrical signals is the fact that some nerves are stimulated by a low frequency signal, such as the pudendal nerve which is stimulated by a frequency on the order of 10-40 Hz. Such a low frequency signal cannot itself pass through body tissue, and therefore is not conducive to direct transdermal application. Many of these challenges have been overcome by the devices described in detail below.

FIG. 1 illustrates schematically an exemplary transdermal signal transmission device 100 in accordance with the present invention. The signal transmitter is preferably contained within a transdermal patch 101 or the like that can be removably secured to the surface of the skin, preferably in the lower abdominal region or lower sacrum of the patient. The patch may be any suitable adhesive bandage or the like, such as the exemplary embodiment shown in FIG. 11 that will be described further below.

Figure 2A:
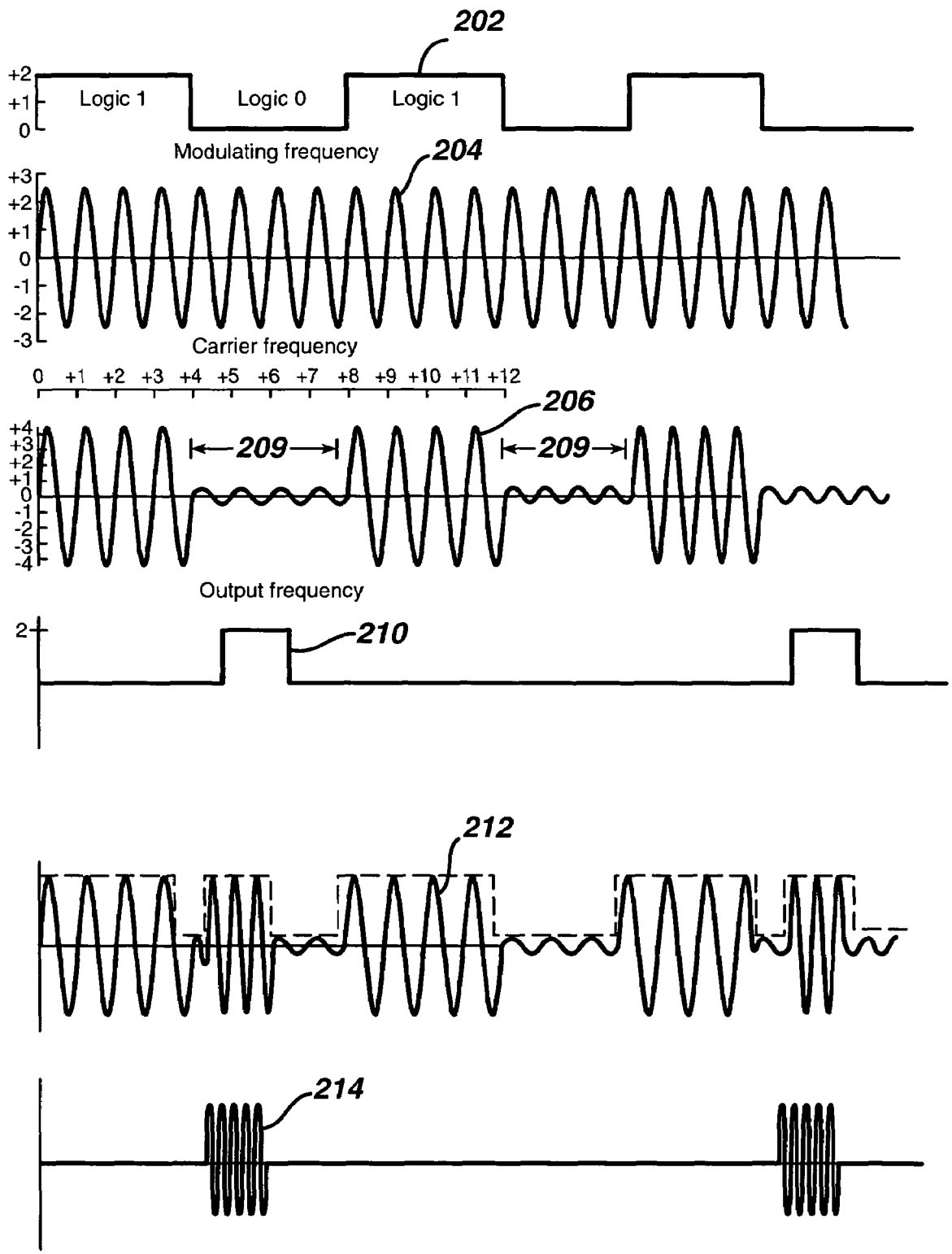
Figure 2B:
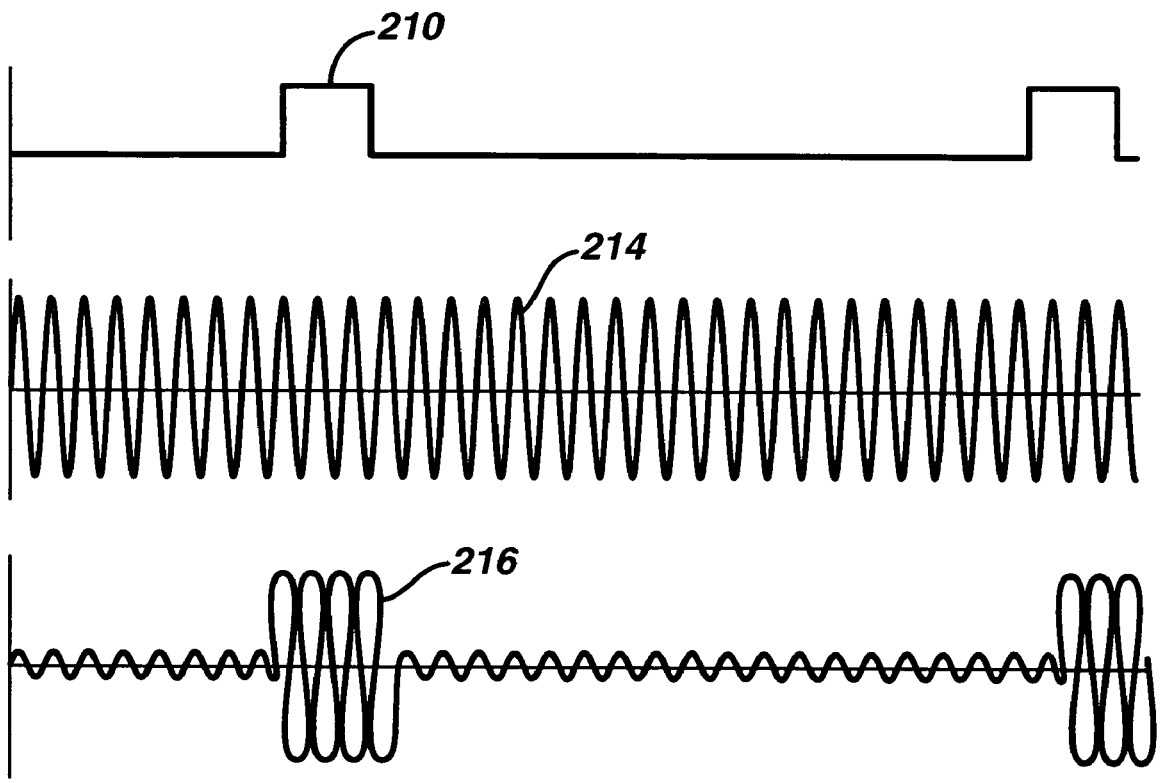

The signal transmitter 100 includes a suitable power source 102 such as a lithium ion film battery by CYMBET™ Corp. of Elk River, Minn., model number CPF141490L, and at least first 104, second 106 and third 107 waveform generators that are electrically coupled to and powered by the battery. These waveform generators may be of any suitable type, such as those sold by Texas Instruments of Dallas, Tex. under model number NE555. The first waveform generator 104 generates a first waveform 202 (see FIG. 2a) or signal having a frequency known to stimulate a first selected body part, such as the pudendal nerve, which is known to be stimulated by a frequency approximately within the range of 10-30 Hz. As indicated above, such a low frequency signal applied to the skin, in and of itself, cannot pass through body tissue to reach the pudendal nerve with sufficient current density to stimulate the nerve. Thus, the second waveform generator 106 is provided to generate a higher frequency carrier waveform 204, which is applied along with the first waveform to an amplitude modulator 108, such as an On-Semi MC1496 modulator by Texas Instruments. The first waveform is preferably a square wave having a frequency of approximately 10-30 Hz, and the second waveform is preferably a sinusoidal signal having a frequency in the range of 10-400 KHz. As those skilled in the art will readily recognize, modulation of this first waveform 202 with the second waveform (carrier waveform) 204 results in a modulated waveform or signal 206 having generally the configuration shown in FIG. 2*a*. The signals shown in FIGS. 2*a* and 2*b* are for illustrative purposes only, and are not intended as true representations of the exemplary signals described herein.

As described in detail in co-pending U.S. patent application Ser. No. 11/146,522, which is incorporated herein by reference in its entirety, this modulated signal 206 can be provided to an appropriate surface electrode 110, such as DURA-STICK Self Adhesive Electrodes from Chattanooga Group, Inc. of Hixson, Tenn., that applies the modulated waveform directly to the skin. As is readily understood by those skilled in the art, the use of the modulated signal enables transmission of the waveform through tissue due to the high frequency nature of the carrier waveform, yet allows it to be detected (and responded to) by the pudendal nerve due to the low frequency envelope of the modulated signal.

Rather than simply applying modulated signal 206 to selectively affect one nerve, the modulated signal 206 has periodic periods of inactivity 209 that can further be taken advantage of to generate a signal package capable of transdermally and selectively stimulating two or more nerves or other body parts. To accomplish this, a third waveform generator 107 generates a third waveform having a frequency different from the first waveform and that is specifically selected to stimulate a second nerve or body part. An exemplary third waveform 210 is shown in FIG. 2. This third waveform must be out of phase with the first waveform 202 to avoid interfering with modulated signal 206. Further, if the frequency ranges that simulate first and second nerves overlap, the third waveform can be generated or applied during the refractory period of the first nerve to ensure the first nerves inability to respond to this subsequent stimulus. The first 202, second 204 and third 210 waveforms are all applied to amplitude modulator 108, which modulates the three waveforms into a modulated signal package 212. The term "signal package" is used herein to describe a single output signal consisting or three or more individual signals modulated together in any way.

As indicated above, the first and third waveform generators generate their respective waveforms 202, 210 out of phase with each other so that when combined with the carrier waveform 204 they appear along separate and discrete portions of the signal package 212, and each of the first and third waveforms have a frequency selected to specifically target different nerves or body portions. For example, the first waveform 202 may have a frequency of 20 Hz, which is known to have an effect on the autonomic element branches of the pudendal nerve which is known to affect overactive bladder, and the third waveform may have a frequency of 10 Hz, which is known to have an effect on the somatomotor branch of the pudendal nerve that is useful in treating intersticial cystitis. To the extent there is an overlap in frequency ranges, the third waveform can be applied during the refractory period of the first nerve as previously stated.

By the system and method described above, individual components of the modulated signal package can be used to selectively target different nerves, different nerve branches, or selected other body parts. That is, a single patch could provide stimulation signals designed to relieve multiple different symptoms such as those associated with overactive bladder, fecal incontinence, interstitial cystitis and any other pelvic floor disorder.

Figure 1A:
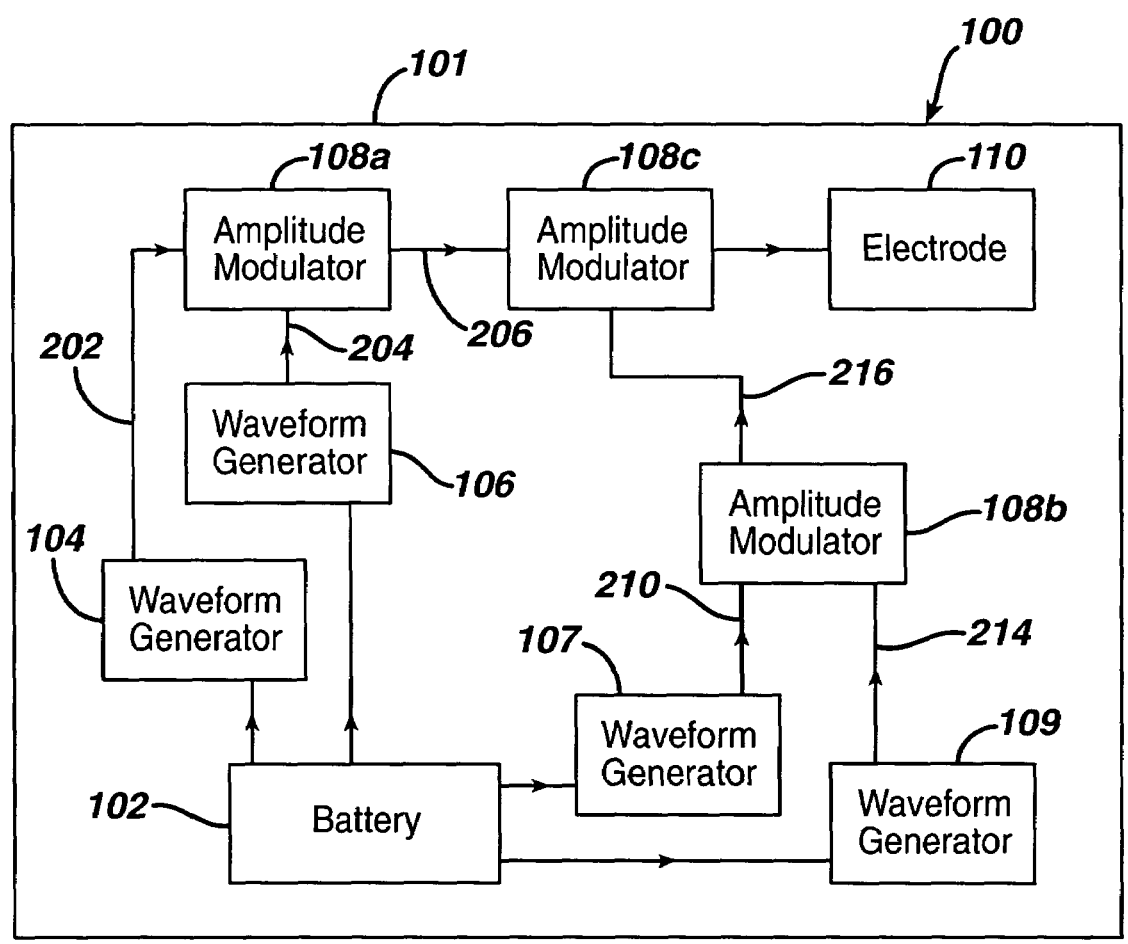

Although one specific embodiment has been described thus far, those skilled in the art will recognize that the appropriate signals may be manipulated in many different ways to achieve suitable modulated signals and/or signal packages. For example, a fourth waveform generator 109 may also be included that generates a fourth carrier waveform 214 having a frequency different from the second carrier waveform. This may be desirable if stimulation of the first and second nerve or body part will require the signal(s) to pass through different types or amounts of tissue. As illustrated, using a single amplitude modulator 108 the fourth carrier waveform 214 must be applied only during periods of inactivity of the first waveform to avoid affecting what would be modulated signal 206. In the alternative, as shown in FIG. 1*a*, the first waveform 202 and second carrier wave 204 may be provided to a first amplitude modulator 108*a* to result in a first modulated waveform as shown as 206 in FIG. 2*b*. Similarly, the third waveform 210 and fourth carrier waveform 214 may be provided to a second amplitude modulator 108*b* to result in a second modulated waveform 216 as shown in FIG. 2*b*. These first and second modulated waveforms may be further modulated by a third modulator 108*c* to create a signal package (i.e., 210) that can be transdermally applied by electrode 110. First and second modulated signals, of course, could also be applied separately via first and second electrodes.

As can be seen from signal package 212, there are still periods of the waveform that are not active. Additional signals can be inserted into these periods to target other frequency independent pudendal nerves or other body parts.

Figure 11:
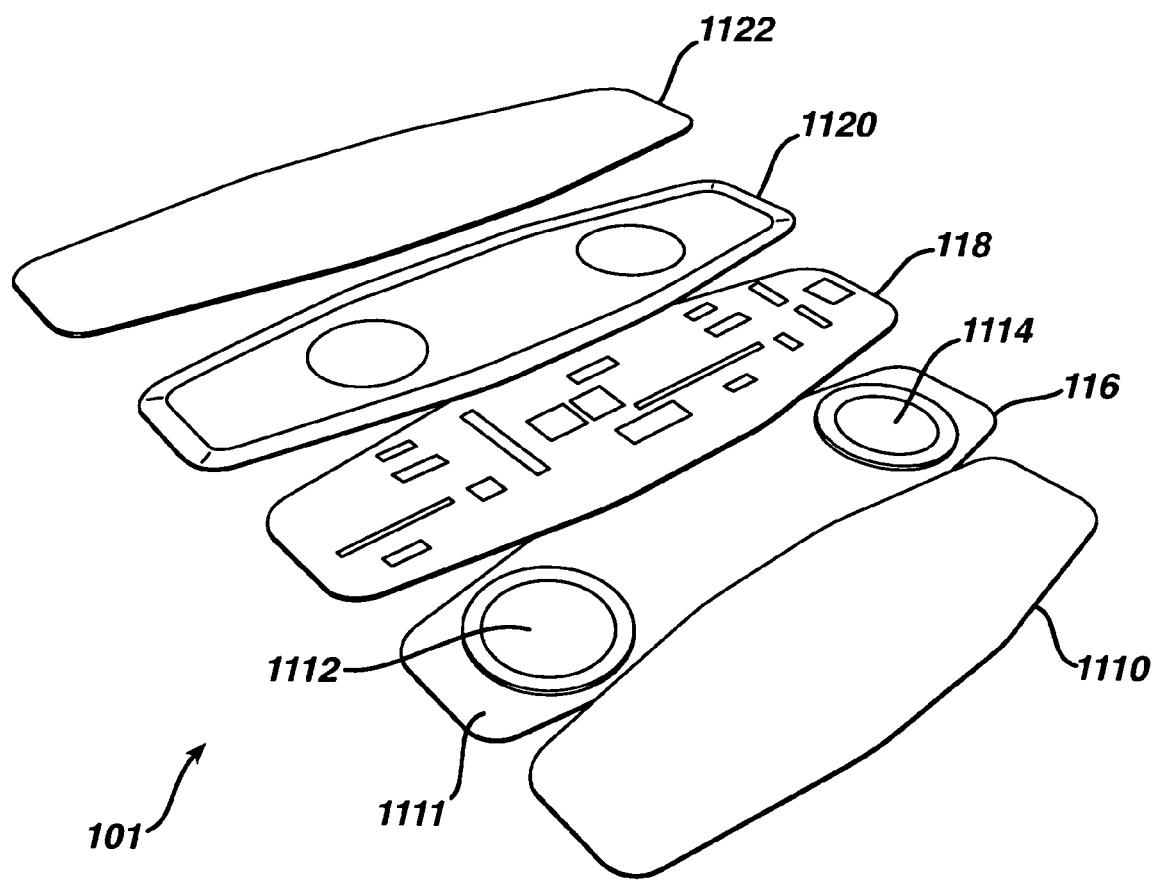
FIG. 11 illustrates one embodiment of a patch within which the devices of the present invention may be incorporated.

Referring now back to FIG. 11, the transdermal stimulation devices described herein may be incorporated into a transdermal patch 101. This patch may include a first layer 1110 having any suitable adhesive on its underside, with the active and return electrodes 1112, 1114 being secured to the top side 1111 of the first layer. The adhesive layer may further include holes therein (not shown) to accommodate the shape of the electrodes and allow direct contact of the electrodes with the surface of the patient's skin. The electrodes may be secured directly to the first layer, or may be held in place by a second layer 1116 comprised of any suitable material such as a plastic. A third layer 1118 consists of a flexible electronics board or flex board that contains all of the electronic elements described above and that is electrically coupled to the electrodes. A fourth layer 1120 is a thin film battery of any suitable size and shape, and the fifth layer 1122 is any suitable covering such as the plastic coverings commonly used in bandages.

Although capable of being applied transdermally only, the conductance of the stimulation energy from the surface electrode to the target nerve can be increased by the placement of a conductive pathway or "tract" that may extend either fully or partially from the surface electrode to the target nerve as illustrated by FIGS. 12*a*-12*c*. The conductive tract may be a cross-linked polyacrylamide gel such as the Aquamid® injectable gel from Contura of Denmark. This bio-inert gel, injected or otherwise inserted, is highly conductive and may or may not be an aqueous solution. The implanted gel provides benefits over rigid implants like wire or steel electrodes. Some of those advantages include ease of delivery, a less invasive nature, and increased patient comfort as the gel is not rigid and can conform to the patient's body. As stated above, the injected gel tract is a highly conductive path from the surface electrode to the target nerve that will further reduce energy dispersion and increase the efficiency of the energy transfer between the surface electrode and the target nerve. The conductive gel pathway may provide a conductive pathway from an electrode positioned exterior of the body (i.e., on the skin) or an electrode positioned under the surface of the skin, both of which are considered to be "in proximity" to the skin.

FIG. 12a illustrates an instance where the conductive gel tract 1201 extends from the transdermal stimulation device positioned on the skin 1200 of a patient to a location closer to the targeted nerve 1202 or nerve bundle. Another advantage of using such a gel material, however, is that unlike rigid conductors (wire), the gel can be pushed into foramina and other recessed areas. Wire or needle electrodes can only come in proximity to one plane of the target nerve, whereas the deformable and flowable gel material can envelope the target nerve as shown in FIG. 12b. That is, the gel tract can be in electrical and physical contact with the full 360 degrees of the target nerve, thereby eliminating conventional electrode alignment issues. Although described above as extending substantially from the transdermal stimulation device to a position closer to the target nerve, the conductive gel tract could also extend from a location substantially in contact with the target nerve, to a location closer to (but not substantially in contact with) the transdermal stimulation device. This type of configuration is illustrated in FIG. 12c. Multiple gel pockets or tracts in any configuration could be used.

Although one suitable conductive gel has been described above, various others are also suitable. Many thermoset hydrogels and thermoplastic hydrogels could be used as well. Examples of thermoset hydrogels include cross-linked varieties of polyHEMA and copolymers, N-substituted acrylamides, polyvinylpyrrolidone (PVP), poly(glyceryl methacrylate), poly(ethylene oxide), poly(vinyl alcohol), poly(acrylic acid), poly(methacrylic acid), poly(N, N-dimethylaminopropyl-N'-acrylamide), and combinations thereof with hydrophilic and hydrophobic comonomers, cross-linkers and other modifiers. Examples of thermoplastic hydrogels include acrylic derivatives such as HYPAN, vinyl alcohol derivatives, hydrophilic polyurethanes (HPU) and Styrene/PVP block copolymers.

The above-described signal transmission devices may also be used in a system that incorporates various biofeedback mechanisms to both create a closed-loop system for treating urge incontinence, but also to provide a system wherein pudendal nerve stimulation is selective, and applied only when necessary as opposed to constantly as has been the case with known attempts at pudendal nerve stimulation. Such a system further includes one or more sensor devices 115 that are preferably implanted within the body. The sensor devices preferably include at least one sensor 120 (FIG. 3) that will sense a selected bio-physiological property, and a data transmission device 122 that transmits data or information gathered by the sensor back outside the body to be further processed as described more fully below.

Figure 3:
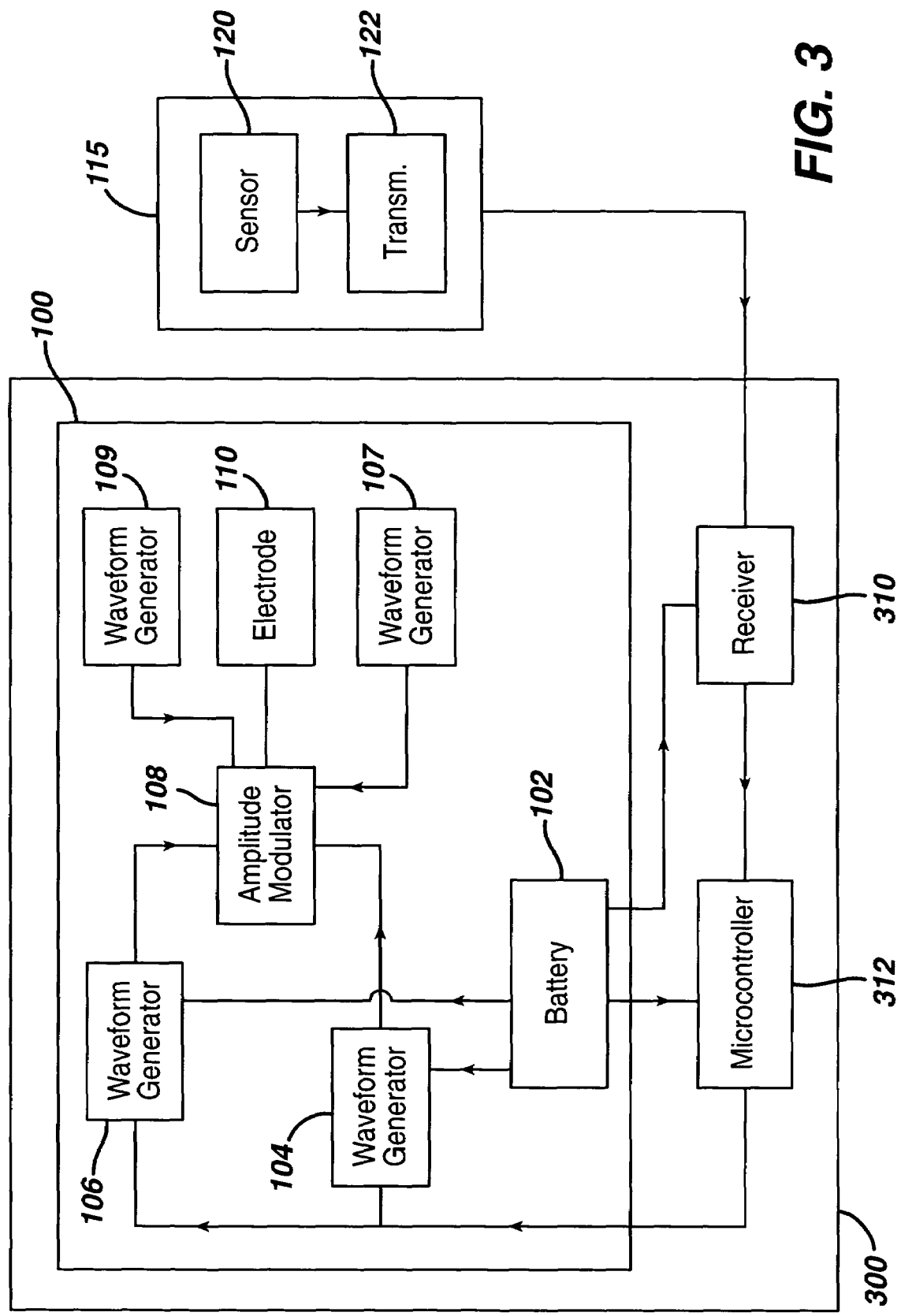
FIG. 3 is a schematic illustration of the device of FIG. 1 further incorporating a biofeedback mechanism.

Referring now to FIG. 3, signal transmitter 100 is part of a larger signal control device 300 that further includes a receiving device 310 such as a MAX1472 from Maxim Semiconductors of Sunnyvale, Calif., that is electrically coupled to and powered by the battery 102. The receiving device receives data from the one or more sensors 115 and provides this data to a microcontroller 312 or the like. The microcontroller is programmed to receive and analyze the data, and based on this data to provide input to the first and second waveform generators 104, 106 to thereby control signal transmission by the signal transmitter 100. For example, the biofeedback sensor 115 may be a pressure sensor that is implanted within the bladder as described in detail below. As pressure measured within the bladder over time is indicative of the existence and magnitude of bladder contractions, when such measurements indicate spastic bladder muscle activity (as compared to normal bladder contractions which will result in a slow and steady rise of pressure within the bladder), a feedback signal can be transmitted to the receiving device and subsequently to the microcontroller. Based on receipt of this signal, the microcontroller will, via control of the waveform generators, cause the electrode to transmit the modulated signal. Receipt of the signal by the pudendal nerve will innervate the bladder muscles to substantially eliminate the spastic muscle contractions.

Figure 4:
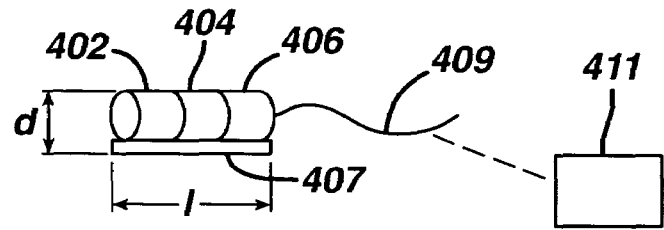
FIG. 4 illustrates an exemplary implantable sensor device that can be used in conjunction with the device of FIG. 3.
Figure 5A:
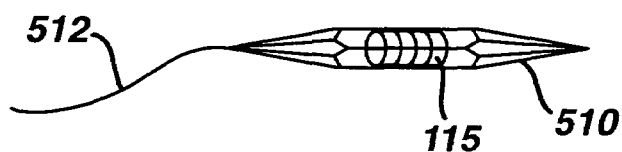
FIG. 5a illustrates the sensor device of FIG. 4 within an expandable cage in its non-expanded state.
Figure 5B:
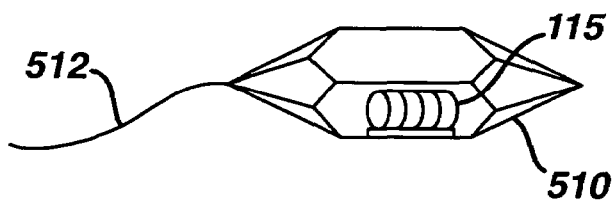
FIG. 5b illustrates the sensor device of FIG. 4 within an expandable cage in the expanded state.

Referring now to FIGS. 4, 5a and 5b, exemplary biofeedback devices 115 will now be described in greater detail. In a preferred embodiment, the implantable biofeedback device 115 consists of multiple electronic components including a power source 402, one or more sensor components 404, and an electronic interface 406, each of which are electrically coupled to one another and mechanically mounted on a printed circuit board 407 in a manner well known in the art. The one or more sensor components 404 sense predetermined physiological properties within the body, and transmit signals or data representing such properties to the electrical interface 406. The system may include a data storage element for storing data correlating to the sensed physiological properties, but may also include a transmitter 409 for transmitting the data external of the patient's body so that it can be used to control generation of the modulated signal as described above. As shown in both FIGS. 5a and 5b, in one embodiment the biofeedback device 115 is substantially surrounded by a collapsible housing 510 or cage.

Preferably, the biofeedback system (exclusive of the housing) has an overall size of about 0.65-10 mm in diameter d, and about 0.65-10 mm in length l. In a preferred embodiment, the sensor component is a micro-miniature piezo-resistive pressure transducer for measuring pressure within a patient's bladder. A suitable transducer is an MPX series pressure sensor from Motorola of Schaumburg, Ill. Other suitable components may include the MSP430F149 microcontroller from Texas Instruments, Inc. of Dallas, Tex. that can be used to acquire, filter and store data from the pressure sensor, and power source such as any suitable biocompatible lithium battery. Although particular suitable electronic components have been named above, many others also exist and could be incorporated into the present invention. As indicated, the electronic components are preferably mounted on printed circuit board. Subsequently, the components and circuit board can be covered or encapsulated in silicone or other suitable covering to protect them from the environment, such as the fluid environment in the bladder Referring now again to the housing 510 as illustrated in greater detail in FIGS. 5a and 5b, in a preferred embodiment the housing is a collapsible cage made of a suitable metal such as Nitonol, stainless steel, or a titanium alloy, or a suitable biocompatible polymer such as polypropylene or polyethylene terapthalate. The collapsible cage is advantageous in that it can exist in a collapsed state shown in FIG. 5a that is sufficiently small to allow insertion through the patient's urethra. Once inserted into the bladder as will be described further below, however, the cage can assume the expanded state shown in FIG. 5b, which has a size sufficiently large so that it cannot pass back into the urethra, and thus will remain in the bladder until physical removal is desired. The housing or cage returns to its expanded state (FIG. 5b) when not compressed by an external force. The electrical components and printed circuit board can be mechanically affixed to the cage in any suitable manner, such as by using a biocompatible adhesive. The housing may further include a tail element 512 extending outwardly therefrom. This tail element 512 may operate as the transmitter for the device in place of the transmitter configuration shown in FIG. 4. As will be further described below, this tail element 512 may also incorporate additional sensor elements if desired.

In another embodiment, the expandable cage may be made of an absorbable material such as Ethisorb® (an absorbable synthetic composite made from polyglactin and polydioxanon) from Ethicon, Inc. of Somerville, N.J., or a combination of absorbable and non-absorbable materials. The absorbable material would preferably dissolve after a predetermined period of time, such as at least 2-3 days, so that the implantable device could be used for temporary data acquisition and subsequently expelled from the body in a non-invasive manner after sufficient data has been gathered.

Figure 6:
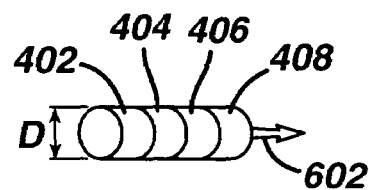
FIG. 6 illustrates an alternate embodiment of an implantable sensor device.

As an alternative to the collapsible cage described above, the housing could have a stable structure rather than a collapsible structure that itself has an outer diameter D that is smaller than the diameter of the urethra to allow insertion therethrough into the bladder (see FIG. 6). The housing may further have one or more projections 602, such as screw threads, barbs or the like, extending outwardly therefrom that can be attached to the sidewall of the bladder by being pushed or driven therein. In yet other alternate embodiments, the implantable device could be sutured to the bladder wall, or adhered thereto using a suitable biocompatible adhesive.

Figure 7A:
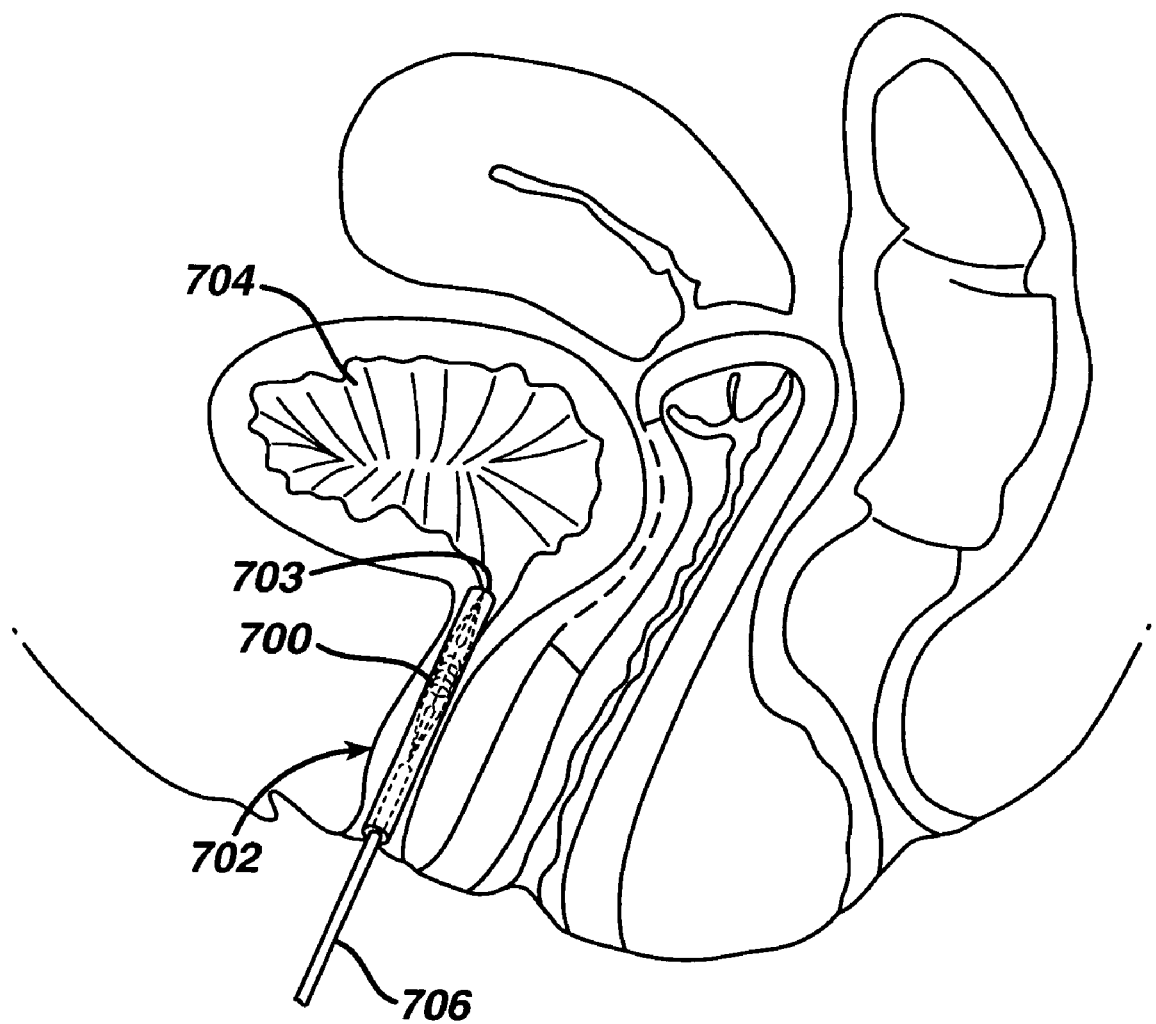
FIGS. 7a-7c illustrate various steps of deployment of the implantable sensor device of FIGS. 5a and 5b.
Figure 7B:
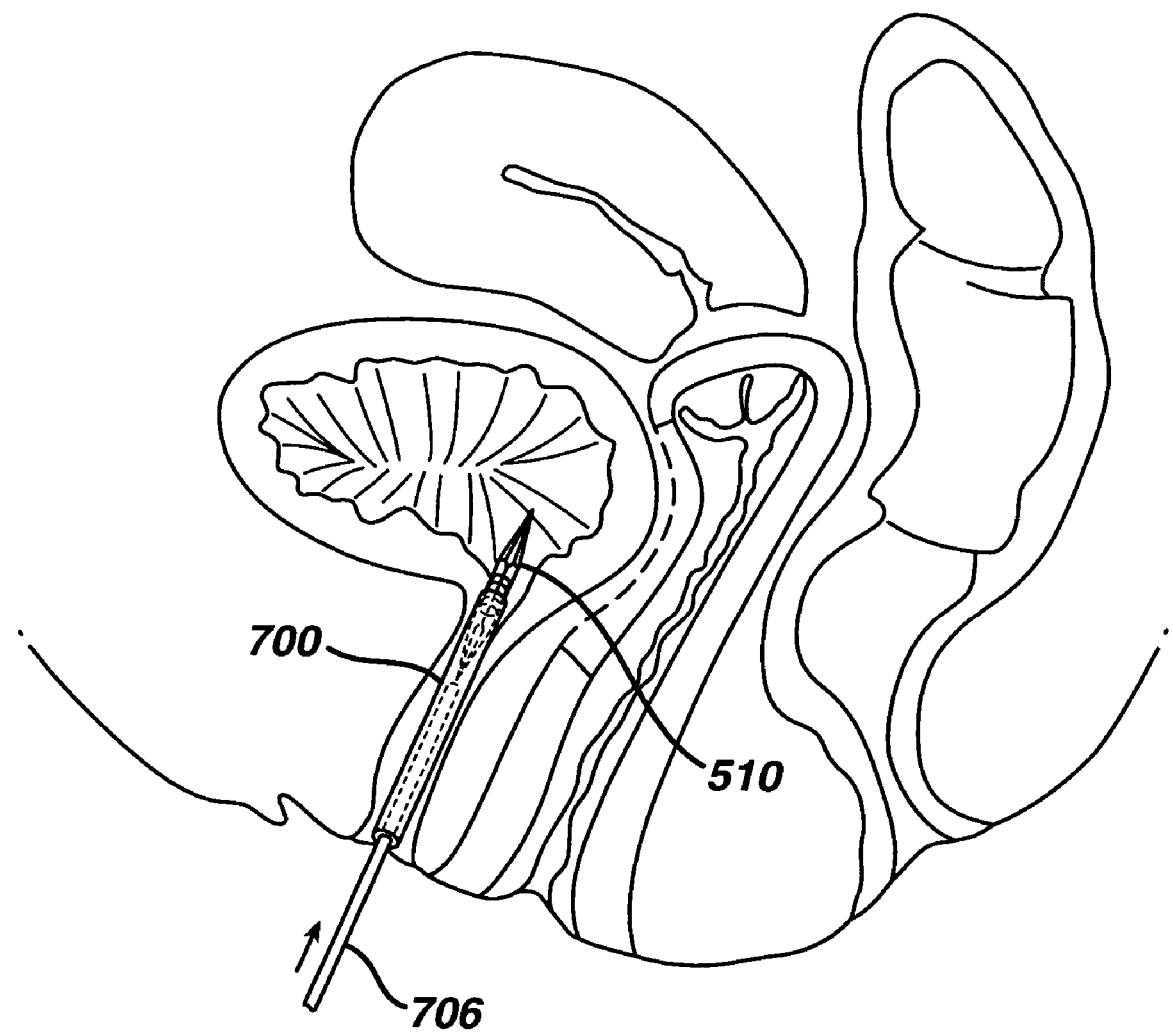
Figure 7C:
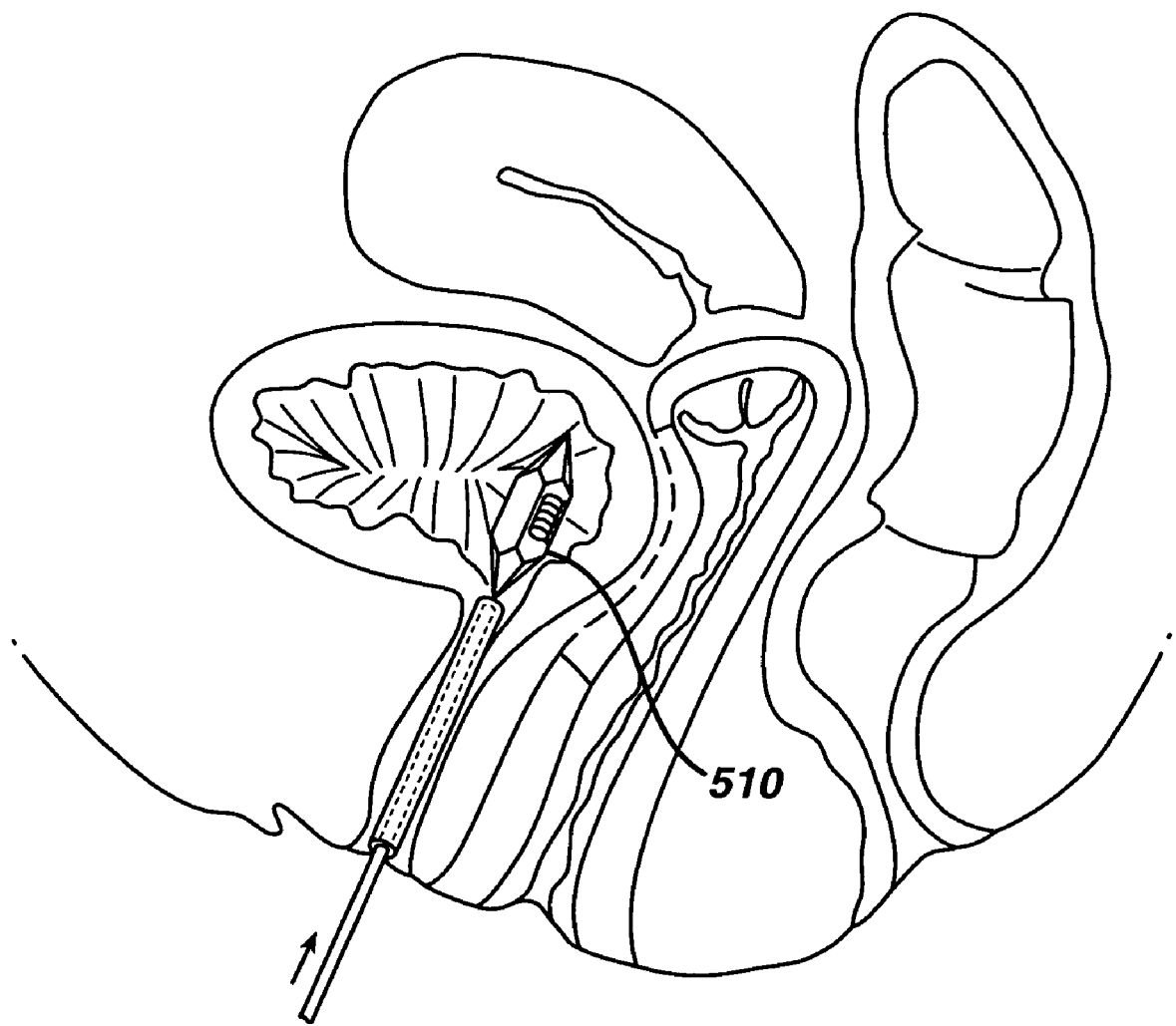
Figure 8:
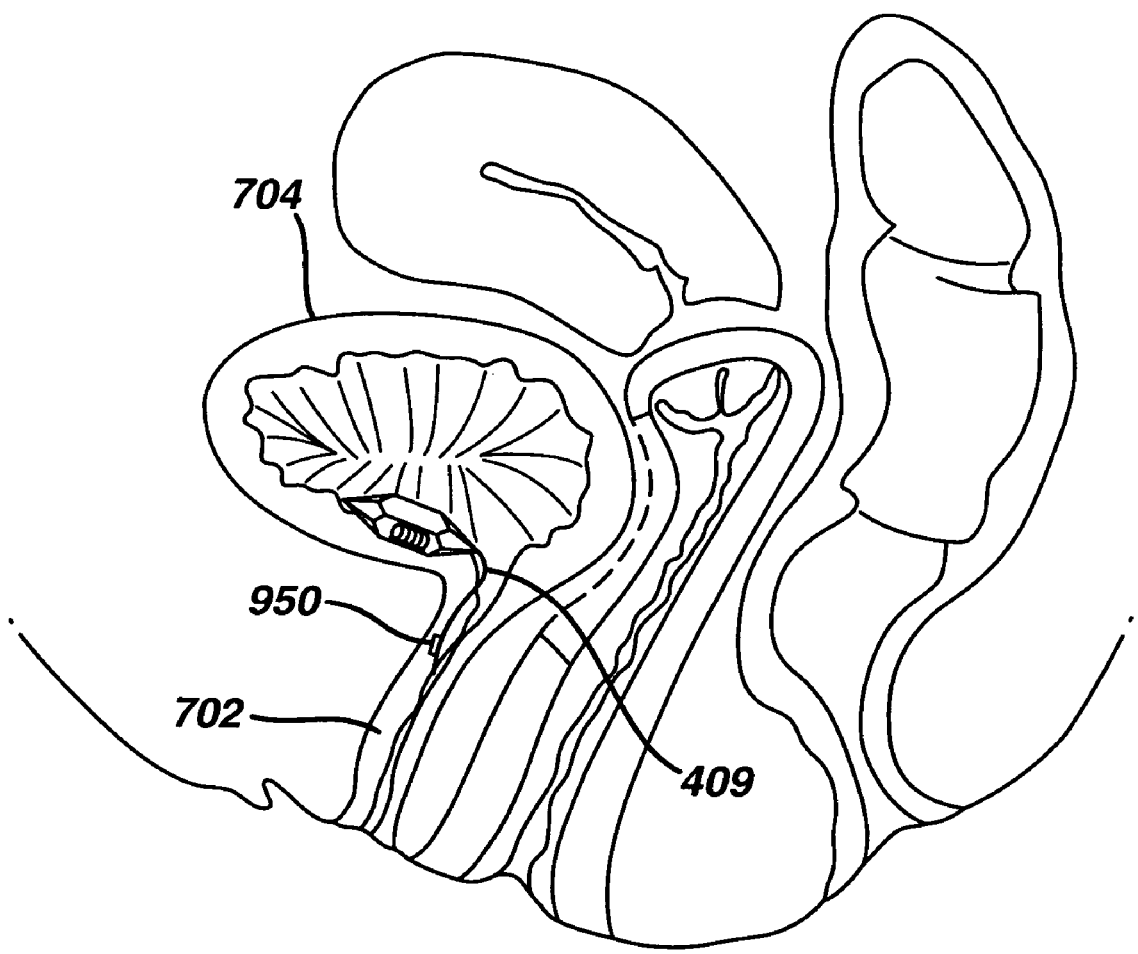
FIG. 8 illustrates the implantable sensor device of FIGS. 5a and 5b deployed within the bladder and having a tail extending into the urethra.

In order to implant the device 115, the housing 510 is compressed and loaded into a single or multi-lumen catheter 700 as shown in FIG. 7a, which is inserted through the urethra 702 until the tip or distal end 703 is positioned within the bladder 704. The catheter may be any catheter suitable for intra-urethral applications, such as a Foley catheter. Fluoroscopy, ultrasound or other similar technology known to those skilled in the art may be used to aid in delivery and placement of the implantable system within the bladder. If a multi-lumen catheter is used, other lumens may be used to fill or drain the bladder, deliver drugs, provide an access for visualization, or monitor pressure while placing the implantable system. An expulsion element 706, such as a push rod or the like is inserted into the primary lumen behind the device and housing, and once the distal end of the catheter is properly positioned within the bladder, the expulsion element is moved toward the distal end of the catheter in the direction of the arrow as shown in FIGS. 7b and 7c to thereby expel the device and housing from the distal end of the catheter and into the bladder. As the implantable system exits the catheter, the collapsible cage 510 is no longer being held in its collapsed state, and proceeds to expand to its fully expanded state. Although use of a catheter is described, other suitable implantation methods may also be used, such as placement via the working channel in a cystoscope or similar surgical tool, or placement via laparoscopic or open surgical methods. Once deployed within the bladder, the expandable cage is dimensioned to prevent the device from being lodged in the bladder neck or otherwise passing into the urethra, but further allows urine to freely flow through it. FIG. 8 illustrates the device fully deployed within the bladder 704.

As mentioned above, alternate embodiments that do not employ expandable cages may also be suitable, such as that shown in FIG. 6. The method of implantation of such devices would be similar to that described above, with the expulsion element within the catheter being used to drive the projecting element 602 into the wall of the bladder to thereby anchor the device to the bladder.

For purposes of the present invention, the device 115 would preferably remain within the bladder for an extended period of time to provide constant feedback used to control operation of the electrode. Where constant feedback is not used (i.e., FIG. 1), the implantable sensors described herein may nevertheless be used to obtain data useful in rendering an accurate diagnosis and/or appropriate treatment. For example, the device could remain within the bladder for 1-2 days, with bladder pressure measurements being taken every ½ second. The type and frequency of bladder pressure changes can be subsequently analyzed to provide feedback to assess urinary function. For example, vesicle pressure measured over time can reveal voiding times and frequency, can provide an indication of an overactive bladder, or of bladder overfilling. In one embodiment, the sensor element(s) are designed to operate in an extended sleep mode, "waking up" at fixed intervals of time to measure pressure or the like. Once sufficient data has been gathered, the device can subsequently be removed from the bladder by inserting a catheter into the bladder to retrieve the implantable device, or using the operating channel of a cystoscope or other suitable instrument to retrieve the device. The catheter or cystoscope would be inserted into the bladder, and the device grasped and pulled back into the catheter or cystoscope channel and subsequently removed from the body.

Under these circumstances, the biofeedback device may further incorporate a data storage device 408 (FIG. 4) in addition to or in place of the transmitter for storing rather than transmitting the data. The data can be subsequently retrieved and manipulated, preferably by uploading the data to a PC based software application in any suitable manner, such as wirelessly, for example, via an infrared data acquisition unit such as ENDEC HSDL-7001 and an IrDA transceiver HSDL-3202 interfaced to the microprocessor, via radiofrequency acquisition, or via a hard wire connection such as through an RS232 interface.

Figure 9:
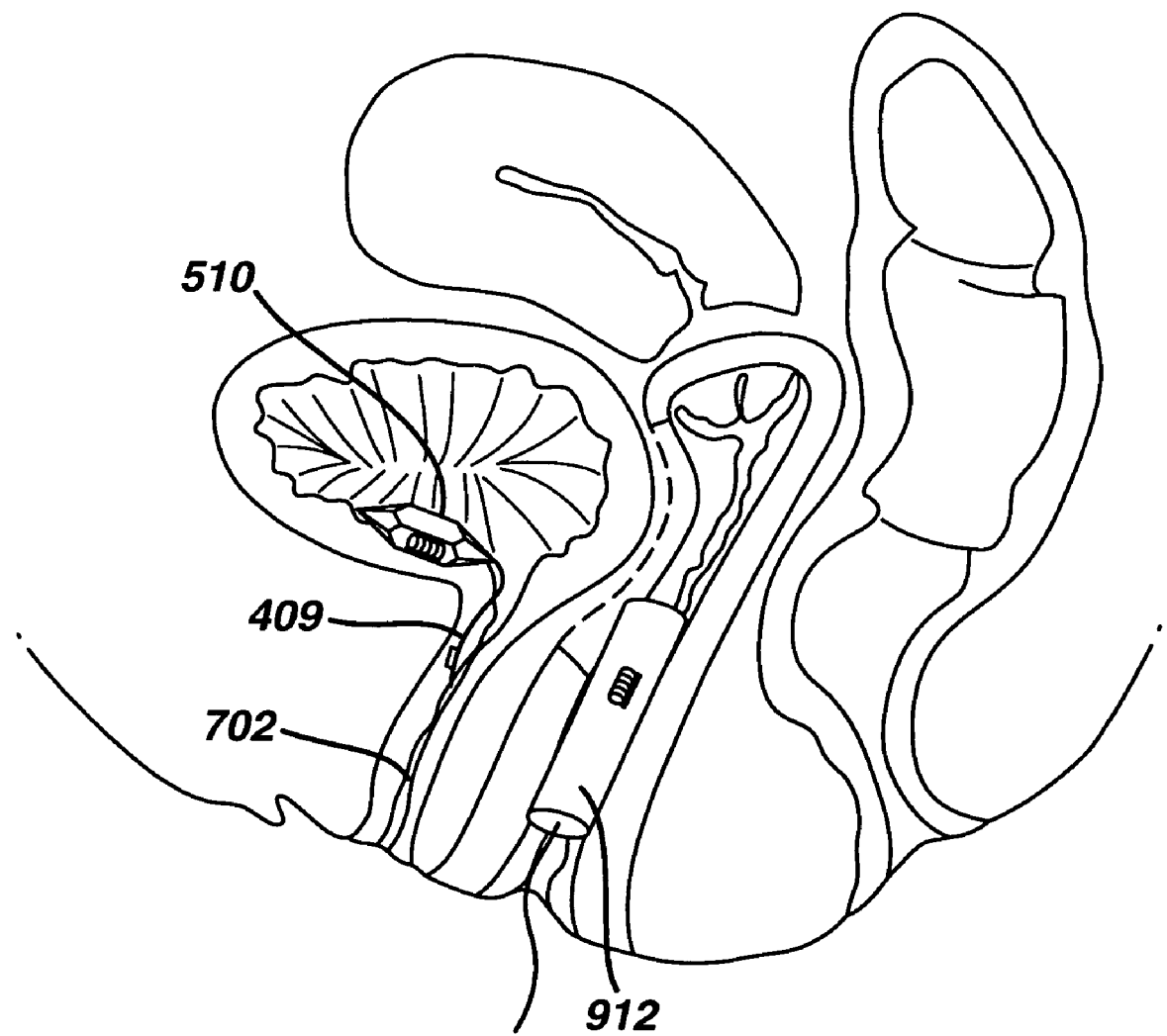
FIG. 9 illustrates first and second implantable sensor devices that can be used in conjunction with the system of FIG. 3.

Referring again to FIG. 3, where biofeedback data is utilized, receiver 310 may receive feedback data from more than one biofeedback device 115. In one embodiment shown in FIG. 9, a second implantable sensor device 902 similar to that shown and described in conjunction with FIG. 4 is designed for insertion into the vaginal canal of a patient, and thus is preferably encapsulated in a "tampon-like" device or casing as shown. This casing 912 is preferably simply rolled up or bound cotton, similar to a tampon. With the second implantable device sensing abdominal pressure, and the first implantable device sensing bladder pressure, the detrusor pressure (pressure of the muscle lining of the wall of the bladder tissue) can be determined by subtracting the bladder pressure from the abdominal pressure. Rises in detrusor pressure will occur if the patient strains, coughs, sneezes, laughs, etc., and detection of these pressures are clinically significant in the diagnosis of various bladder and lower urinary tract disease states. For example, the frequency of detrusor pressure increases provides meaningful data for assessing urge incontinence.

In an alternate embodiment, one of the two implantable devices transmits data to the other, which then wirelessly transmits both sets of data to receiver 310.

Figure 10A:
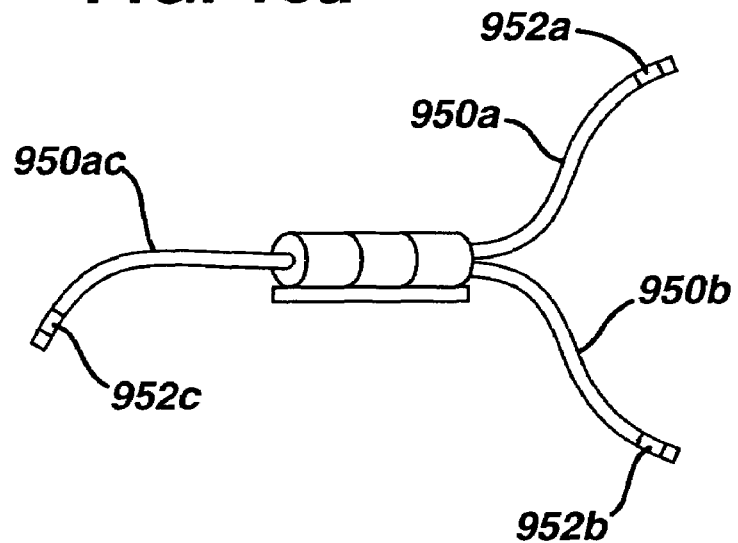
FIG. 10a illustrates yet another embodiment of an implantable sensor device.
Figure 10B:
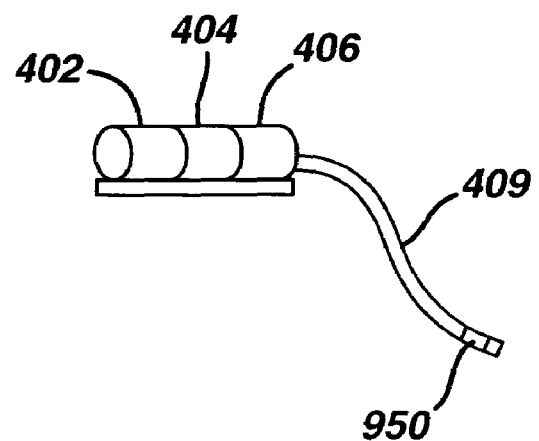
FIG. 10 illustrates an alternate embodiment of an implantable sensor device.

In yet another embodiment, the first implantable device within the bladder further includes one or more additional sensors 950 that are incorporated into one or more tail elements, as shown in FIGS. 10 and 10a. In one particular implementation, the sensor(s) are leak detection sensors incorporated into a tail that is designed to extend from the device within the bladder, through the sphincter and into the urethral canal 702 as shown in FIG. 8. This sensor(s) detect the presence of fluid, and thus will detect leakage of urine such as occurs in a stress incontinent patient, while at the same time the pressure sensor within the bladder measures bladder pressure. Thus, stress incontinence episodes can be recorded by correlating time at which a rise in bladder pressure occurs concurrently with detection of fluid leakage through the urethra.

Further, multiple tail elements 950*a*, 950*b*, 950*c* may incorporate multiple sensor elements 952*a*, 952*b*, 952*c* as shown in FIG. 10*a* to record the pressure at different points in the bladder, and thus provide more accurate readings.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A method for electrically stimulating a pudendal nerve of a mammal, comprising:
    placing at least one electrode in proximity to the mammal's skin in an abdominal or sacral region of the mammal;
    injecting an electrically conductive gel into the body of the mammal so as to form a conductive gel pathway extending at least partially along a distance between the at least one electrode and the pudendal nerve; and
    stimulating the pudendal nerve by applying an electrical signal via the electrode that travels, at least in part, through the conductive gel pathway, wherein the electrode is positioned within a patch device having an adhesive thereon for securing it to the skin.

2. The method according to claim 1, wherein the conductive gel pathway extends substantially the entire distance between the electrode and the pudendal nerve.

3. The method according to claim 1, wherein the conductive gel substantially envelopes the pudendal nerve.

4. The method according to claim 1, wherein the conductive gel is bio-inert.

5. The method according to claim 1, wherein the conductive gel remains flexible following injection.

6. The method according to claim 1, wherein the conductive gel is a cross-linked polyacrylamide gel.

7. The method according to claim 1, wherein the injecting step is performed using a syringe.

8. A method for electrically stimulating a pudendal or sacral nerve of a mammal, comprising:
    placing at least one electrode in proximity to the mammal's skin substantially in the abdominal or sacral regions of the mammal;
    injecting an electrically conductive gel into the body of the mammal so as to form a conductive gel pathway extending at least partially along a distance from the at least one electrode to the pudendal or sacral nerve; and
    stimulating the pudendal or sacral nerve by applying an electrical signal via the electrode that travels, at least in part, through the conductive gel pathway, wherein the electrode is positioned within a patch device having an adhesive thereon for securing it to the skin.

9. The method according to claim 8, wherein the conductive gel pathway extends substantially the entire distance between the electrode and the pudendal or sacral nerve.

10. The method according to claim 8, wherein the conductive gel pathway substantially envelopes the pudendal or sacral nerve.

11. The method according to claim 8, wherein the conductive gel is bio-inert.

12. The method according to claim 8, wherein the conductive gel remains flexible following injection.

13. The method according to claim 8, wherein the conductive gel is a cross-linked polyacrylamide gel.

14. The method according to claim 8, wherein the injecting step is performed using a syringe.

15. A method for treating a pelvic condition of a female patient comprising:
    providing a transcutaneous electrical stimulation device including an electrode adapted to apply an electrical waveform to the patient's skin;
    identifying a location for placing the stimulation device that is substantially in the patient's abdominal or sacral regions;
    creating a conductive pathway along at least a portion of a distance from the identified location to the patient's pudendal or sacral nerve by injecting a conductive gel along said pathway;
    placing the stimulation device in the identified location; and
    stimulating the pudendal or sacral nerve by activating the electrode to thereby apply the electrical waveform to the patient's skin, wherein the electrical waveforms is conducted, at least in part, through the conductive pathway.

* * * * *

UNITED STATES PATENT AND TRADEMARK OFFICE
CERTIFICATE OF CORRECTION

| | | |
|---|---|---|
| PATENT NO. | : 7,647,112 B2 | Page 1 of 1 |
| APPLICATION NO. | : 11/344285 | |
| DATED | : January 12, 2010 | |
| INVENTOR(S) | : Michael R. Tracey et al. | |

It is certified that error appears in the above-identified patent and that said Letters Patent is hereby corrected as shown below:

On the title page, item [54] and Column 1, line 1: replace the title with "SYSTEM AND METHOD OF STIMULATING A PUDENDAL OR SACRAL NERVE USING A CONDUCTIVE GEL PATHWAY."

Signed and Sealed this

Thirty-first Day of August, 2010

David J. Kappos
*Director of the United States Patent and Trademark Office*